United States Patent
Rothe et al.

(10) Patent No.: US 7,144,741 B2
(45) Date of Patent: Dec. 5, 2006

(54) PROCESS AND APPARATUS FOR THE DETERMINATION OF PARAMETERS OF A BREATH CONDENSATE

(76) Inventors: Michael Rothe, Jacobsohnstr. 19, Berlin (DE) 13088; Joachim Porzelt, Langer Weinberg 3, Eibelstadt (DE) 97246; Claudia Lehmann, Edelwaisstr. 37, Berlin (DE) 13158; Gunther Becher, Froöbelweg 33, Schönow (DE) 16312; Stefan Dietze, Birkenwerderweg 39, Lehnitz (DE) 16565

( * ) Notice: Subject to any disclaimer, the term of this patent is extended or adjusted under 35 U.S.C. 154(b) by 820 days.

(21) Appl. No.: 10/085,390

(22) Filed: Feb. 28, 2002

(65) Prior Publication Data

US 2003/0023389 A1    Jan. 30, 2003

(30) Foreign Application Priority Data

Jul. 30, 2001   (DE)   ................................ 101 37 565

(51) Int. Cl.
   *G01N 1/28*   (2006.01)
(52) U.S. Cl. ........................................ 436/180; 436/174
(58) Field of Classification Search ................ None
   See application file for complete search history.

(56) References Cited

U.S. PATENT DOCUMENTS

| 5,104,813 | A | * | 4/1992 | Besemer et al. ............ 436/179 |
| 5,399,486 | A | * | 3/1995 | Cathey et al. ............... 435/7.9 |
| 5,863,502 | A | * | 1/1999 | Southgate et al. ............ 422/58 |
| 6,010,459 | A | * | 1/2000 | Silkoff et al. ................ 600/532 |
| 6,033,368 | A | * | 3/2000 | Gaston et al. ............... 600/532 |
| 6,148,657 | A | * | 11/2000 | Satoh et al. ................ 73/23.35 |
| 6,190,326 | B1 | * | 2/2001 | McKinnon et al. .......... 600/529 |
| 6,585,661 | B1 | * | 7/2003 | Hunt et al. .................. 600/532 |

FOREIGN PATENT DOCUMENTS

| DE | 199 51 204 | 5/2001 |
| WO | WO 97/35519 | 10/1997 |

* cited by examiner

*Primary Examiner*—Jeffrey R. Snay
(74) *Attorney, Agent, or Firm*—Stephan A. Pendorf; Akerman Senterfitt

(57) ABSTRACT

The invention relates to a process and apparatus for the determination of the parameters of a breath condensate using at least one sensor for the measurement of the parameters and an analysis unit with display for the measurement results. The at least one sensor (2) is positioned in a closed cassette (1), whereby the cassette includes storage containers (4, 5, 6) with flushing solutions and/or solutions for the conditioning of the at least one sensor and/or calibration solutions and/or compounds for the manufacture of a calibration solution and/or for the dilution of the sample solution and/or for elevation of the ion concentration or the conductivity of the sample solution. The storage containers (4, 5, 6) deliver their contents completely or in metered amounts into the cassette and/or onto the at least one sensor (2) under the action of means acting from the outside and through the cassette walls. Furthermore, the cassette (1) includes at least one opening for the introduction of the sample solution onto the at least one sensor (2), and has contacts (3) for receiving the measurement data originating from the at least one sensor (2).

7 Claims, 1 Drawing Sheet

Fig.: 1
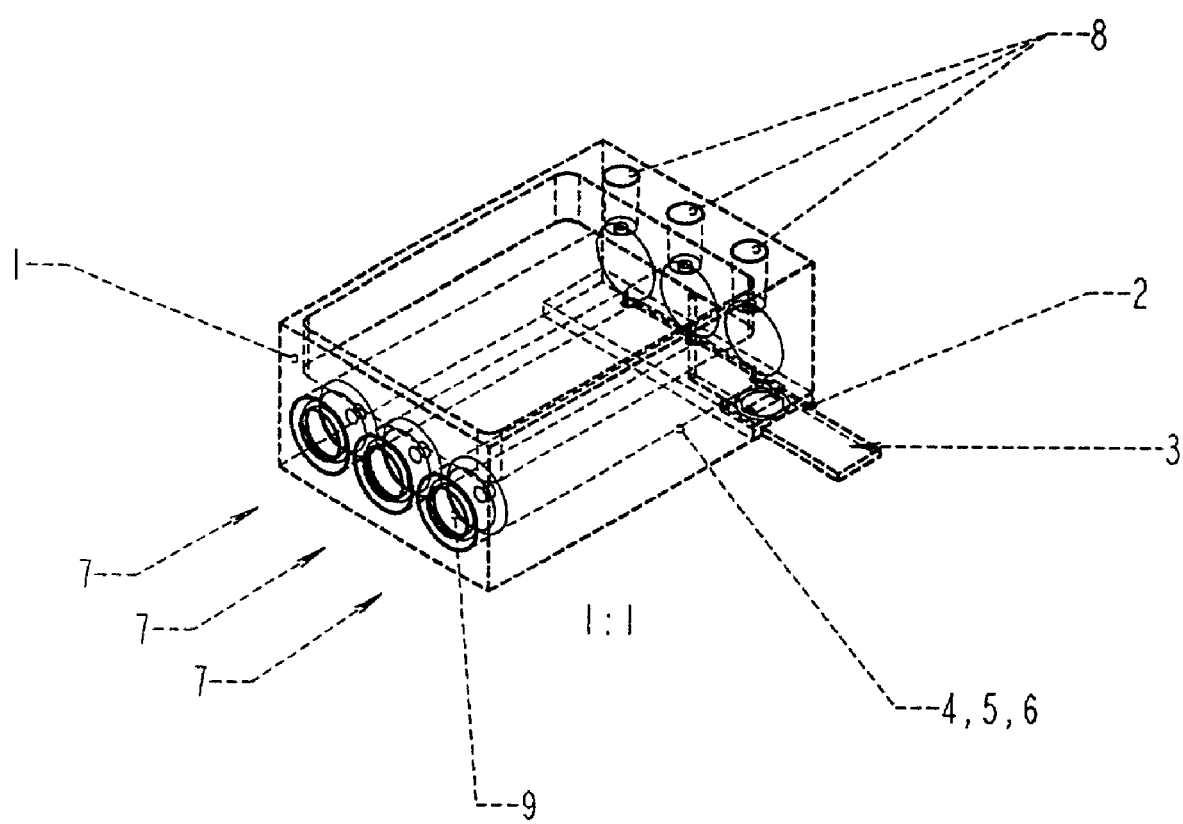

PROCESS AND APPARATUS FOR THE DETERMINATION OF PARAMETERS OF A BREATH CONDENSATE

FIELD OF THE INVENTION

The invention relates to processes and apparatus for the determination of selected parameters or a breath condensate.

BACKGROUND ART

Processes and apparatus for the determination of parameters of breath condensates are known.

DE 199 51 204 A1 discloses a process and apparatus for the analysis of the contents of exhaled air, wherein a breath condensate produced from the exhaled air is subjected to analysis and the result displayed. The amount of breath condensate obtained from the exhaled air is measured and after achievement of a preselected sample amount a direct determination of the contained substances is carried out by measurement of individual and/or combined parameters by way of electro-chemical sensors. The amount is thereby that part which is captured in a filter or a storage layer, which is removed from a filter or a storage layer by a micro-dosing system, which causes a complete filling or saturation of a filter or a storage layer, or which diffuses through a filter or a storage layer.

It is a disadvantage of this and other solutions that their practical application in routine diagnostics is limited due to the need for concentration and measurement of very small amounts of materials. To this is added the danger of contamination of the sample, the disinfection cost after each analysis and the danger of infection.

SUMMARY OF THE INVENTION

It is now an object of the invention to automate as much as possible the analysis of the contents of the exhaled air and to thereby significantly reduce the disinfection cost as well as the danger of infection and to allow no contamination of the sample. This object is achieved with a process in accordance with the invention wherein the breath condensate is measured in a cassette with at least one sensor and a storage container for at least one solution required for the measurement.

In a preferred embodiment of the process of the invention for the determination of parameters of a breath condensate by use of one or more sensors for measurement of the parameters and an analysis unit with a display for the measurement results, the measurement is carried out within a closed cassette in which the at least one sensor is located and solutions are dispensed from storage containers of the cassette and/or placed onto the sensor or sensors by influence on the storage containers from outside the cassette. The solutions preferably cause flushing of the cassette and/or a conditioning of the at least one sensor and/or a calibration of the at least one sensor, and/or contribute to the dilution of the sample solution, and/or to an increase of its ion concentrations or conductivity. The sample solution is preferably applied onto the at least one sensor through an opening of the cassette and the measurement results originating from the sensor or sensors are preferably transmitted to outside the cassette and transferred from there to an analysis unit.

After determination of the parameters of the breath condensate of the sample solution the cassette is preferably disposed of without the solutions required for the measurement including the sample solution leaving the cassette.

By appropriate selection of the sensors and solutions for the execution of the process, cassettes for different applications can be industrially manufactured and made available to the user.

In order to allow very different applications, a preferred embodiment of the invention provides for the mixing of solutions or solids and solutions prior to their delivery into the cassette or application onto the at least one sensor. This is preferably achieved by connecting the storage containers.

A typical case is the production of a calibration solution within the cassette by mixing the contents of two or more connected storage containers under the influence of an external force.

In a variant, a blister containing a lyophilized enzyme as dry matter or another reactive substance can be used which mediates a quantitatively defined reaction in the calibration solution that produces an analyte. Preferred analytes are, for example, short lived bio-molecules and hydrogen peroxide.

The invention provides different variations for the dispensing of the solutions from the storage containers by way of means external to the cassette. This can be achieved with syringe shaped storage containers by operation of the piston, in flexibly constructed storage containers by squeezing of the respective storage container, or by destruction of the flexible container walls. This is preferably carried out in the cassette receptacle of an apparatus, which is provided with suitable means for acting on the storage containers. When the cassettes are appropriately standardized, only one apparatus for carrying out the process running in the cassette is needed.

The sample solution is preferably sucked into the cassette or is injected thereinto. It is also provided in accordance with the invention, that the sample solution prior to the introduction thereof into the cassette is diluted with a buffer solution or a diluting solution, or is adjusted to an ion concentration or conductivity necessary for the measurement.

For ensuring the quality of the measurement, the process provides that the control of the temperature of the at least one sensor is coordinated with the one of the sample solution, in particular the temperature of the sample solution is adapted to the working temperature of the at least one sensor.

It is furthermore preferred for quality assurance that apart from the pure measurement results the process data within the cassette are captured and made available for analysis, such as flow, temperature, freedom from air bubbles, time.

In a further preferred embodiment of the invention, it is provided that the storage containers are constructed as a sleeve into which cartridges can be inserted, whereby the cartridges are filled with a solution selected from the group of flushing solutions, solutions for the conditioning of the at least one sensor, calibration solutions and/or compounds for the manufacture of a calibration solution and/or for the dilution of the sample solution and/or for the elevation of the ion concentration or the conductivity of the sample solution. The cartridges are preferably inserted into the storage containers to deliver their contents completely or in metered amounts into the cassette or onto the at least one sensor, by way of means which act on the cartridges from the outside through the cassette walls. The delivery can take place analogously as described above for the storage containers.

In a special embodiment in accordance with the invention, the outlets of at least one of the storage containers the cartridges into the cassette are closed by a common or individual valves and that the valves can be moved under external control into an open position.

BRIEF DESCRIPTION OF THE DRAWINGS

An apparatus in accordance with the invention for the carrying out of the process with the use of one or more sensors for the measurement of the parameters and an analysis unit with display for the measured data will be described in more detail in the following with reference to the drawing of FIG. 1, which shows a schematic wire cage drawing of the apparatus of the invention.

DETAILED DESCRIPTION OF THE PREFERRED EMBODIMENTS

FIG. 1 shows that the at least one sensor 2 is positioned in a closed cassette 1. This can be achieved permanently or by way of an insert into the cassette 1. Furthermore, the cassette 1 includes storage containers 4, 5, 6 with flushing solutions and/or solutions for conditioning of the at least one sensor 2 and/or with solutions for calibration and/or with compounds for the manufacture of a calibration solution and/or for the dilution of the sample solution and/or the elevation of the ion concentration or the conductivity of the sample solution. The storage containers 4, 5, 6 are emptied by means 7 which act on them from outside through the cassette walls, whereby their content is dispensed completely or in metered amounts into the cassette and/or onto the at least one sensor 2. The cassette further has at least one opening 8 for introduction of the sample solution onto the at least one sensor 2. Solutions which are not contained in the storage containers 4, 5, 6 can also be introduced through this at least one opening 8.

Contacts 3 for output of the measurement signals originating from the at least one sensor 2 are provided on the outside of the cassette 1.

The storage containers 4, 5, 6 are inserts into the cassette or are an integral part of the cassette 1 which is then refillable, or they are sleeves into which cartridges including the solutions can be inserted.

In the illustrated embodiment, the storage containers 4, 5, 6 are syringe shaped and the means 7 acting through the cassette walls operate the syringe piston 9. The storage containers 4, 5, 6 are therefor positioned with their end directly on or in the wall of the cassette 1 and closed by the syringe piston 9.

For execution of the process, the cassette 1 is preferably inserted into a cassette receptacle which at the support locations for the syringe pistons 9 includes individually controlled push rods with a linear drive. When these push rods are moved towards the cassette 1, they force the respectively associated syringe piston 9 into the storage container 4, 5, 6 and the solution contained therein through an exit opening in the respective storage container 4, 5, 6 arrives in the cassette 1 or directly on the at least one sensor 2.

After determination of the parameters of the breath condensate, the control pistons are retracted and the cassette 1 can be removed from the cassette receptacle for disposal.

In another embodiment (not illustrated), the storage containers 4, 5, 6 are of flexible construction. The means 7 acting thereon through the cassette walls then cause a squeezing out of the respective storage container 4, 5, 6 or a destruction of the flexible walls. The latter can be achieved by rupturing a seam.

In order to prevent contact of the operating means 7 with the solutions, it is preferably provided that the cassette walls in the regions where they are penetrated by the means 7 acting on the storage containers 4, 5, 6 are provided with an elastic layer which forms an insulating layer between the operating means 7 and the storage containers 4, 5, 6 or the solutions in the cassette 1. It can be pushed into the cassette 1 during the squeezing out or destruction of the storage containers 4, 5, 6.

In order to mix certain solutions, or solutions and other compounds prior to delivery thereof into the cassette 1, for example, to produce certain properties of a solution, the invention also provides that the storage containers 4, 5, 6 are divided into separate sub containers and that the means 7 acting from the outside through the cassette walls on the storage containers 4, 5, 6 first cause a mixing of the substances from the sub-containers.

For example, a storage container 4 is preferably provided which contains a lyophilized enzyme as dry compound or another reactive substance which mediates a quantitatively defined reaction when introduced into the calibration solution.

Furthermore, it is provided in one embodiment of the invention that the cassette and/or the cassette receptacle has a cooling and/or heating arrangement for control of the working temperature.

It is possible with the present invention to automate as much as possible the analysis of the components of exhaled air and to thereby prevent contamination of the sample and to significantly reduce the disinfection cost and danger of infection.

The invention claimed is:

1. Process for the determination of parameters of a breath condensate by using at least one sensor for the measurement of the parameters and an analysis unit with display of the measurement results, comprising the steps of
    delivering a solution from a storage container and applying said solution onto the at least one sensor within a closed cassette including the at least one sensor by action on the storage container from outside the cassette on the storage containers, the solution generating at least one of
    a cassette flushing;
    a conditioning of the at least one sensor;
    a calibration of the at least one sensor; and
    a dilution of a sample solution and/or elevation of the ion concentration or conductivity;
    applying through an opening of the cassette a breath condensate sample solution onto the at least one sensor for parameter determination; and
    coordinating the temperature of the at least one sensor with a temperature of the sample solution during determination of the parameters of the breath condensate, by adjusting the temperature of the sample solution to the working temperature of the at least one sensor;
    transmitting measurement results originating from the at least one sensor out of the cassette and to the analysis unit
    whereby data apart from the pure measurement data, selected from the group consisting of flow rate, temperature, freedom from air bubbles and, time are captured and transmitted to the analysis unit; and
    disposing the cassette after the determination of parameters of the breath condensate and of a sample solution without release of any solution in the cassette.

2. Process according to claim 1, wherein the sample solution is sucked or injected into the cassette, preferably from a sample container or a sample collector system.

3. Process according to claim 1, wherein prior to the delivery of the sample into the cassette or the application thereof onto the at least one sensor, a mixing of the substances in the storage containers is carried out by action from outside the cassette.

4. Process according to claim 1, wherein a calibration solution is produced by mixing the contents of two or more interconnected storage containers in the cassette by action applied from outside the cassette and the calibration solution is then delivered into the cassette or applied onto the at least one sensor.

5. Process according to claim 4, wherein a blister is used which contains a lyophilized enzyme as dry matter, or another compound which generates a quantitatively defined reaction in the calibration solution by which an analyte is created.

6. Process according to claim 1, wherein the delivery of the solutions from the storage containers by action applied from outside the cassette is carried out by using syringe shaped storage containers and operation of syringe pistons of the storage containers or by using storage containers of flexible construction and squeezing out of the respective container or by destruction of the flexible walls.

7. Process according to claim 1, comprising the further step of diluting the sample solution prior to introduction into the cassette with a buffer solution or a dilution solution or adjusting an ion concentration or conductivity necessary for the measurement.

* * * * *